(12) United States Patent
Zhou et al.

(10) Patent No.: US 11,491,173 B2
(45) Date of Patent: Nov. 8, 2022

(54) PHARMACEUTICAL COMPOSITION AND APPLICATION THEREOF

(71) Applicant: TASLY PHARMACEUTICAL GROUP CO., LTD., Tianjin (CN)

(72) Inventors: Shuiping Zhou, Tianjin (CN); He Sun, Tianjin (CN); Yiqian Zhang, Tianjin (CN); Xiaohui Ma, Tianjin (CN); Jiawen Shi, Tianjin (CN); Yi He, Tianjin (CN); Xinxin Li, Tianjin (CN); Jing Wang, Tianjin (CN); Xiaoqing Li, Tianjin (CN); Lijun Fan, Tianjin (CN); Jingjing Zhang, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 73 days.

(21) Appl. No.: 16/976,832

(22) PCT Filed: Apr. 4, 2019

(86) PCT No.: PCT/CN2019/081505
§ 371 (c)(1),
(2) Date: Aug. 31, 2020

(87) PCT Pub. No.: WO2019/192599
PCT Pub. Date: Oct. 10, 2019

(65) Prior Publication Data
US 2021/0000853 A1    Jan. 7, 2021

(30) Foreign Application Priority Data

Apr. 4, 2018 (CN) .......................... 201810302178.X

(51) Int. Cl.
*A61K 31/7048* (2006.01)
*A61P 9/04* (2006.01)
*A61K 31/216* (2006.01)
*A61K 31/343* (2006.01)
*A61K 31/405* (2006.01)
*A61K 31/704* (2006.01)

(52) U.S. Cl.
CPC ........ *A61K 31/7048* (2013.01); *A61K 31/216* (2013.01); *A61K 31/343* (2013.01); *A61K 31/405* (2013.01); *A61K 31/704* (2013.01); *A61P 9/04* (2018.01)

(58) Field of Classification Search
CPC .............. A61K 31/7048; A61K 31/216; A61K 31/343; A61K 31/405; A61K 31/704; A61P 9/04
USPC ....................................................... 514/26
See application file for complete search history.

(56) References Cited

U.S. PATENT DOCUMENTS 9,211,310 B2 * 12/2015 Zhang ................. A61K 36/258

FOREIGN PATENT DOCUMENTS

| CN | 1919235 A | 2/2007 |
|---|---|---|
| CN | 1919237 A | 2/2007 |
| CN | 101085018 A | 12/2007 |
| CN | 101912441 A | 12/2010 |
| CN | 102362971 A | 2/2012 |
| CN | 103385920 A | 11/2013 |
| CN | 103520270 A | 1/2014 |
| CN | 104096014 A | 10/2014 |
| CN | 104147032 A | 11/2014 |
| CN | 104274518 A | 1/2015 |
| CN | 104274520 A | 1/2015 |
| CN | 104415045 A | 3/2015 |
| CN | 106421293 A | 2/2017 |
| CN | 101239099 A | 8/2018 |

OTHER PUBLICATIONS

Wang et al. Global Chemome Study by LC Coupled with DAD and ESI-Q-TOF MS of a Composite Traditional Chinese Medicine Qishenyiqi Dropping Pills. Chromatographia 2010, 72, September (No. 5/6): 431-440. (Year: 2010).*
Zhang et al. Tanshinones: Sources, Pharmacokinetics and Anti-Cancer Activities. Int. J. Mol. Sci. 2012, 13, 13621-13666. (Year: 2012).*
Wang et al. Five new sesquiterpenoids from Dalbergia odorifera. Fitoterapia 95 (2014) 16-21. (Year: 2014).*
International Patent Application No. PCT/CN2019/081505; Int'l Search Report; dated Jul. 9, 2019; 4 pages.
European Patent Application No. 19781789.3; Extended Search Report; dated Dec. 13, 2021; 9 pages.
Zheng et al.; "The Mechanism Research of Qishen Yiqi Formula by Module-Network Analysis"; Evidence-Based Complementary and Alternative Medicine; vol. 2015 Article ID 497314; Jan. 2015; 12 pages.
Han et al.; "Absorption, metabolism and effect of compatibility on absorption of qishenyiqi dropping pill"; Biomedical Chromatography; vol. 28; 2014; p. 554-563.
"Study on the multi-dimensional fingerprinting of qi-shen-yi-qi dropping pills"; Electronic Journal, Medical Health Technology; Series 2012; Thesis; Jul. 2012; 95 pages. (contains English Abstract, p. 7 and 8).

* cited by examiner

*Primary Examiner* — Yih-Horng Shiao
(74) *Attorney, Agent, or Firm* — BakerHostetler

(57) ABSTRACT

Disclosed are a pharmaceutical composition and an application thereof. The pharmaceutical composition of the present invention comprises the following components in parts by weight: 2-20 parts of phenolic acids, 0.5-5 parts of flavonoids, 0.005-0.5 part of tanshinones, 5-20 parts of saponins, and 10-18 parts of volatile oils. The pharmaceutical composition has the functions of protecting against myocardial damage and treating heart failure.

19 Claims, 3 Drawing Sheets

Figure 1-Sham operation group

Figure 1-Model group

Figure 1-Drug group of the present invention

Figure 1-Comparison drug group

Figure 2-Sham operation group

Figure 2-Model group

Figure 2-Drug group of the present invention

Figure 2-Comparison drug group

Figure 3-Sham operation group

Figure 3-Model group

Figure 3-Drug group of the present invention

Figure 3-Comparison drug group

PHARMACEUTICAL COMPOSITION AND APPLICATION THEREOF

CROSS-REFERENCE TO RELATED APPLICATIONS

This application is the National Stage of International Patent Application No. PCT/CN2019/081505 filed Apr. 4, 2019, which claims priority from Chinese Patent Application No. 201810302178.X, filed Apr. 4, 2018, the disclosures of each of which are incorporated herein by reference in their entireties for any and all purposes.

FIELD OF THE INVENTION

The present invention relates to the medical field, particularly to a pharmaceutical composition and use thereof.

BACKGROUND OF THE INVENTION

Heart failure, which is called "HF" for short, refers to a situation in which venous return cannot be fully discharged from the heart due to the disorders in systolic function and/or diastolic function of the heart, resulting in blood stasis in the venous system and insufficient blood perfusion in the arterial system, consequently leading to cardiac circulatory disorder syndrome, which manifests as pulmonary congestion and vena cava congestion. Heart failure is the end stage of the development of heart disease instead of a separate disease. Heart failure mostly begins with left heart failure, namely firstly manifesting as pulmonary congestion.

Heart failure can be divided into systolic heart failure and diastolic heart failure according to the difference in left ventricular ejection fraction (LVEF). Epidemiological studies have shown that 40% to 71% of patients with chronic heart failure belong to diastolic heart failure (DHF), which mostly occurs in the elderly, females, and those with high blood pressure and/or diabetes.

DHF was named as heart failure with preserved left ventricular ejection fraction (HF-PEF) in the Guidelines for Heart Failure in 2008 by the European Society of Cardiology (ESC). For a long time, more attention has been paid to left ventricular systolic heart failure in clinical work. Patients with heart failure with normal left ventricular ejection fraction account for about 50% of the total patients with heart failure. The prognosis of heart failure with normal left ventricular ejection fraction is not better than that of systolic heart failure, and the rate of sudden death thereof is high.

| Heart failure type | Heart failure with preserved ejection fraction (HFpEF) | Heart failure with reduced ejection fraction (HFrEF) |
| --- | --- | --- |
| LVEF | ≥50% | ≤40% |
| Original definition | Diastolic heart failure | Systolic heart failure |
| Percentage of patients | 50% (22% to 73%) | 50% |
| Average diagnosis time of new patients | 8.3 ± 3.3 years | 6.6 ± 3.6 years |
| Sex | Mostly women | Mostly men |
| Relevant factor | Age | — |
| Medical treatment | The diagnosis of HF-PEF is challenging, and effective treatment is not yet clear. | Randomized clinical trials mainly include patients with HFrEF, and effective treatment has been confirmed. |

Heart failure with preserved left ventricular ejection fraction is caused by impaired active relaxation ability of ventricular during diastole and impaired filling of left ventricular during diastole resulting from increased myocardial stiffness, and the incidence of this type of heart failure has been rising in recent years. Since heart failure with preserved left ventricular ejection fraction often occurs in early heart failure clinically, and earlier than contractile dysfunction, it slows the course and progression of HF-PEF, and can alleviate the patient's pain and reduce the patient's financial burden.

The current treatments of HF-PEF include active control of blood pressure, correction of atrial fibrillation, control of atrial fibrillation ventricular rate, and application of diuretics, ACEI, β-blockers for reversing left ventricular hypertrophy and improving diastolic function. However, in clinical practice, the effects after the above medical treatments are still dissatisfied in some patients, resulting in a significant decrease in quality of life.

The phenolic acid derivatives as traditional Chinese drugs are widely distributed in the medicinal plants, e.g. Honeysuckle (*Lonicera japonica* Thunb.), the root of *Rubus crataegifolius* (Rosaceae), composite Dandelion and breviscpini, Labiatae *Salvia officinalis*, *Canarium bengalense* (Burseraceae) and Umbelliferae *Angelica Sinensis* and *Rhizoma Ligustici Chuanxiong* etc. More and more attentions have been paid to the pharmacological activities that were found in the phenolic acid derivatives of these plants, for example scavenging free radicals, anti-inflammation, anti-virus, regulating immune, anti-coagulation and anti-tumor etc.

Usually, the phenolic acid derivatives are categorized as follows: the benzoic-acid-based phenolic acids, for example, *Dioscorea bulbifera* L and Dandelion; the cinnamic-acid-based phenolic acids, for example, the ferulic acid, a chief bio-active component in the water-soluble extract of *Angelica Sinensis*, *Rhizoma Ligustici Chuanxiong* and Dandelion; the lithospermic acid that is isolated from *Salvia Miltiorrhiza* Bunge (Fam. Labiatae); the phenylacetic-acid-based phenolic acids, for example the p-hydroxyphenylacetic acid found in Dandelion and the fruit of *Forsythia suspense*.

Tanshinone, also known as the total tanshinones, is the bacteriostatic fat-soluble phenanthraquinone extracted from Danshen, a traditional Chinese drug (the root of *Salvia Miltiorrhiza* Bunge, Fam. Labiatae). More than 10 compounds have been identified, including the tanshinone I, tanshinone IIA, tanshinone IIB, cryptotanshinone and isocryptotanshinone etc. Wherein, 5 compounds of cryptotanshinone, dihydrotanshinone II, hydroxytanshinone, methyl tanshinate and tanshinone IIB are confirmed to have an antibacterial effect, as well as effects of anti-inflammation and lowering temperature. Sodium tanshinone IIA sulfonate, a sulfonation product of tanshinone IIA, is water-soluble and clinically proven to have a significant effect on treating angina pectoris and little side effects. It has been developed into a new drug for treating coronary heart disease (CHD). Multiple effects have been found in the total tanshinones in anti-bacterium, diminishing inflammation, activating blood circulation to dissipate blood stasis and promoting wound repair, and there are no significant side effects after a long term of administration.

Saponin is a glucoside, which has triterpene or spirostane aglycones and is mainly distributed in terrestrial higher plants. The main active components in various Chinese herbs, such as the Ginseng, Balloonflower and Bupleurum include saponin. Saponin has the bioactivities of anticancer, inhibiting proliferation of tumor cells, inducing apoptosis, affecting signal transduction of cancer cells, and inhibiting tumor angiogenesis and metastasis of tumor cells. Also, saponin has the effects of lowering blood sugar and blood lipid, anti-virus and immunoregulation, becoming a very popular research subject at home and abroad.

Flavonoids originally refer to a class of 2-phenyl-chromone-based compounds, and now generally refer to a class of chemical substances with two benzene rings connected to each other through a three-carbon chain between them. The main natural flavonoids can be classified according to the oxidation degree of the three-carbon chain between the A ring and the B ring, the connection position of the B ring, and whether the three-carbon chain forms a ring, and other characteristics. Flavonoids are a class of secondary metabolites of plants, and have various biological activities such as antioxidant, anti-angiogenesis, anti-inflammatory, antiviral, lowering blood sugar and blood lipid, anti-osteoporosis. They are widely distributed in vegetables, fruits and other plants. Studies have shown that the intake of rich flavonoids in the diet will reduce the risk of colon cancer, prostate cancer, breast cancer and other cancers.

Volatile oils as traditional Chinese drugs are mainly derived from aromatic traditional Chinese drugs. It is a general term for a class of volatile oil-like components that are immiscible with water and can be obtained by steam distillation. Volatile oils are widely present in plants, and it can almost be said that all odorous plants contain volatile oils of varying amounts. Plants with higher volatile oil contents mainly include: Compositae, Rutaceae, Lauraceae, Labiatae, Umbelliferae, Myrtaceae, Ericaceae, Gramineae, Zingiberaceae, Leguminosae, Rosaceae, Magnoliaceae, Liliaceae, Cupressaceae etc.

Volatile oils are mainly composed of terpenoids and aromatic compounds and the oxygen-containing derivatives thereof, such as alcohols, aldehydes, ketones, phenols, ethers, lactones, etc. In addition, nitrogen-containing and sulfur-containing compounds are also included. Volatile oils are colorless or light yellow transparent oily liquid that can volatilize at room temperature, and have the effects of anti-inflammatory, anti-allergy, anti-microbial, anti-mutation, anti-cancer, anthelmintic effects, enzyme inhibitory effects, and effects on the central nervous system, respiratory system, etc.

In the prior art, there is no report about a medicament with a combination of salvianolic acids, tanshinones, saponins, flavonoids, and volatile oils. There is also no report that these components combined according to a certain ratio can be used to treat heart failure.

SUMMARY OF THE INVENTION

In order to solve the above technical problems, the present invention provides a pharmaceutical composition.

The present invention also provides use of the pharmaceutical composition in the treatment of heart failure.

The present invention is achieved through the following technical solutions:

The present application provides a pharmaceutical composition, comprising the following components:

| | |
|---|---|
| Phenolic acids | 2-20 parts by weight |
| Flavonoids | 0.5-5 parts by weight |
| Tanshinones | 0.005-0.5 part by weight |
| Saponins | 5-20 parts by weight |
| Volatile oils | 10-18 parts by weight. |

Further, the present application provides a pharmaceutical composition, comprising the following components:

| | |
|---|---|
| Phenolic acids | 4-18 parts by weight |
| Flavonoids | 0.8-4 parts by weight |
| Tanshinones | 0.01-0.3 part by weight |
| Saponins | 6-18 parts by weight |
| Volatile oils | 14-17 parts by weight. |

Furthermore, the present application provides a pharmaceutical composition, comprising the following components:

| | |
|---|---|
| Phenolic acids | 6-16 parts by weight |
| Flavonoids | 1-3 parts by weight |
| Tanshinones | 0.05-0.2 part by weight |
| Saponins | 8-16 parts by weight |
| Volatile oils | 15-16 parts by weight. |

In the above pharmaceutical compositions, the phenolic acids comprise substances of the following weight parts: Danshensu (i.e., salvianic acid A): protocatechuic aldehyde: salvianolic acid T:salvianolic acid U:salvianolic acid D:salvianolic acid G:rosmarinic acid:lithospermic acid:salvianolic acid B:salvianolic acid A:isosalvianolic acid C=(3.0-11.0):(0.06-0.15):(0.2-0.55):(0.2-0.55):(0.4-1.3):(0.02-0.05):(0.3-0.8):(0.05-0.40):(0.10-0.40):(0.07-0.12):(0.015-0.04).

In the above pharmaceutical compositions, the flavonoids comprise substances of the following weight parts: calycosin-7-glucoside:ononin:calycosin:formononetin=(0.6-1.8):(0.3-0.7):(0.03-0.18):(0.03-0.65).

In the above pharmaceutical compositions, the tanshinones comprise substances of the following weight parts: dihydrotanshinone I:cryptotanshinone:tanshinone I:tanshinone IIA=(0.001-0.03):(0.005-0.04):(0.002-0.025):(0.004-0.03).

In the above pharmaceutical compositions, the saponins comprise substances with the following weight parts: notoginsenoside R1:ginsenoside Rg1:ginsenoside Rb1: astragaloside:ginsenoside Rd=(1.8-3.5):(2.5-5.4):(1.3-5.0):(0.30-0.60): (0.4-0.6).

In the above pharmaceutical compositions, the volatile oils comprise substances with the following weight parts: trans-nerolidol:nerolidol oxide=(25-38):(55-76). Wherein, the nerolidol oxide comprises (3R,6S,7R)-3, 7,11-trimethyl-3,7-epoxy-1,10-dodecadien-6-ol, (3R,6R,7S)-3, 7,11-trimethyl-3,7-epoxy-1,10-dodecadien-6-ol, (3S,6R,7S)-3, 7,11-trimethyl-3,6-epoxy-1,10-dodecadien-7-ol and (3S,6S,7R)-3, 7,11-trimethyl-3,6-epoxy-1,10-dodecadien-7-ol, with the weight parts of (3-6):(4-7):(25-33):(23-30).

In the pharmaceutical composition of the present invention, the phenolic acids (Danshensu, protocatechuic aldehyde, salvianolic acid T, salvianolic acid U, salvianolic acid D, salvianolic acid G, rosmarinic acid, lithospermic acid, salvianolic acid B, salvianolic acid A, isosalvianolic acid C), tanshinones (dihydrotanshinone I, cryptotanshinone, tanshinone I, tanshinone IIA), saponins (notoginsenoside R1, ginsenoside Rg1, ginsenoside Rb1, astragaloside, ginsenoside Rd), flavonoids (calycosin-7-glucoside, ononin, calycosin, formononetin) can be prepared by the prior art, obtained by extraction and refinement, or obtained commercially. The volatile oil, trans-nerolidol belongs to prior art. (3R,6S,7R)-3,7,11-trimethyl-3,7-epoxy-1,10-dodecadien-6-ol, (3R,6R,7S)-3,7,11-trimethyl-3,7-epoxy-1,10-dodecadien-6-ol, (3S,6R,7S)-3,7,11-trimethyl-3,6-epoxy-1,10-dodecadien-7-ol and (3S,6S,7R)-3,7,11-trimethyl-3,6-epoxy-1,10-dodecadien-7-ol also belong to prior art, such as "Tao Y, Wang Y. Bioactive sesquiterpenes isolated from the essential oil of *Dalbergia odorifera* T. Chen [J]. Fitoterapia, 2010, 81(5): 393-399.".

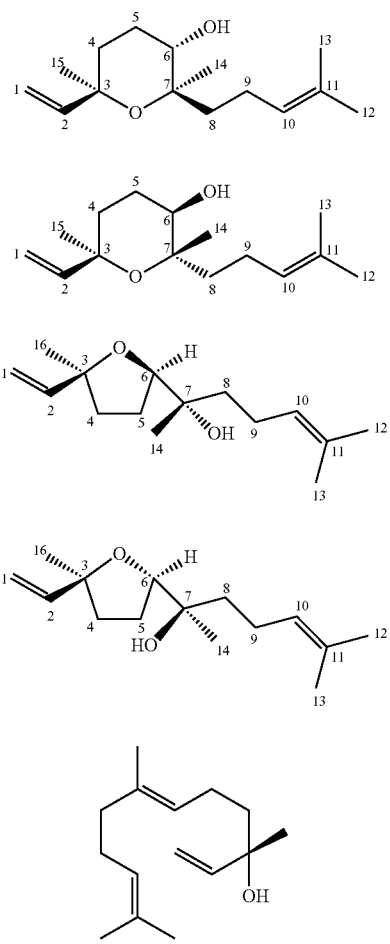

F1: rel-(3R,6S,7R)-3,7,11-trimethyl-3,7-epoxy-1,10-dodecadien-6-ol
F2: rel-(3R,6R,7S)-3,7,11-trimethyl-3,7-epoxy-1,10-dodecadien-6-ol
F3: rel-(3S,6R,7S)-3,7,11-trimethyl-3,6-epoxy-1,10-dodecadien-7-ol
F4: rel-(3S,6S,7R)-3,7,11-trimethyl-3,6-epoxy-1,10-dodecadien-7-ol
F5: trans-nerolidol.

In an embodiment of this invention, the present invention further provides a pharmaceutical preparation comprising the pharmaceutical composition of the present invention. In a preferred embodiment, as active ingredients, the pharmaceutical composition accounts for 0.1~99.9 wt % of the pharmaceutical preparation, and the balanced is pharmaceutically acceptable carrier(s). In another embodiment of this invention, the pharmaceutical composition is prepared in the form of unit dosage, and said unit dosage refers to individual preparation, e.g. each tablet of tablets, each capsule of capsules, each bottle of oral solutions and each bag of granules etc.

The preparation is suitable to be administrated orally, parenterally (including be administrated subcutaneously, e.g. injections or reservoir-type tablets; intradermally; intrathecally; intramuscularly, e.g. the reservoir; and intravenously etc.), rectally, and topically (e.g. sublingually). The most suitable administration route, however, depends on the condition of patients.

In the context of this invention, the pharmaceutical carriers used are various kinds of organic or inorganic carriers that can be administrated in combination with the pharmaceutical composition, e.g. excipients, lubricants, adhesives, disintegrants and coating agents used for solid preparations; or pharmaceutical additive, e.g. colorants and sweetening agents. Said carriers are selected from: sugar alcohol, e.g. mannitol, sorbitol, xylitol; amino acid, e.g. cysteine hydrochloride, methionine, glycine; Vitamin C; EDTA disodium, EDTA calcium disodium salt; inorganic salts, e.g. monovalent alkali carbonate, acetate, phosphate or the aqueous solutions thereof; sodium chloride, potassium chloride, sodium pyrosulfite, sodium bisulfite, sodium thiosulfate; calcium carbonate, calcium bicarbonate; stearate, e.g. calcium stearate, magnesium stearate; inorganic acids, e.g. hydrochloric acid, acetic acid, sulfuric acid, phosphoric acid; organic acid salts, e.g. sodium lactate; oligosaccharide, polysaccharide, cellulose and the derivatives thereof, e.g. maltose, glucose, fructose, dextran, sucrose, lactose, cyclodextrin (such as β-cyclodextrin), starch; silicon derivatives; alginate; gelatin; polyvinylpyrrolidone; glycerol; agar; surfactants, e.g. Tween-80; polyethylene glycol; phospholipids materials; Kaolin; talc powder etc.

The pharmaceutical preparation of the present invention can be in any pharmaceutically acceptable dosage forms, including tablets, such as sugar-coated tablets, film-coated tablets and enteric-coated tablet; capsules, such as hard capsules and soft capsules; oral solutions; buccal tablets; granules; instant powders; pills; powders; pastes; pellets; suspensions; pulvis; solutions; injections; suppositories; pastes, such as ointments, hard plasters; creams; sprays; drops; and patches. Preferably, the preparations of the present invention are in the following dosage forms: oral dosage forms, such as capsules, tablets, oral solutions, granules, pills, powders, pellets and pastes etc.; and injections, such as powders for injection, injection liquids, infusion etc. Most preferably, the preparations of the present invention are tablets.

The preparations with oral dosage forms can include commonly used excipients, adhesives, bulking agents, diluents, tablet-pressing agents, lubricants, disintegrating agents, colorants, flavoring agents, and wetting agents. If necessary, the tablets can be coated.

Suitable exemplary bulking agents include cellulose, mannitol, lactose and other analogous bulking agents.

Preferable examples of excipients include: lactose, D-mannitol, D-sorbitol, starch, e.g. α-starch, dextrin, crystalline cellulose, low-substituted hydroxypropyl cellulose, sodium carboxymethyl cellulose, arabic gum, amylopectin, light anhydrous silicic acid, synthetic aluminum silicate and aluminum magnesium silicate, etc.

Preferable examples of lubricants include: magnesium stearate, calcium stearate, talc powder, silica gel and sodium dodecyl sulfate, etc.

Preferable examples of adhesives include: α-starch, sucrose, gelatin, arabic gum, methylcellulose, carboxymethyl cellulose, sodium carboxymethyl cellulose, crystalline cellulose, sugar, D-mannitol, trehalose, dextrin, amylopectin, hydroxypropyl cellulose, hydroxypropyl methyl cellulose and pyrrolidone.

Preferable examples of disintegrating agents include: lactose, sugar, starch, carboxymethyl cellulose, calcium carboxymethyl cellulose, sodium alkylamide, sodium carboxymethyl starch, light anhydrous silicic acid, low-substituted hydroxypropyl cellulose, starch, polyvinylpyrrolidone, and sodium starch glycollate, etc.

Preferable examples of coating agents include: hydroxypropyl methyl cellulose, hydroxypropyl cellulose, ethylcellulose, carboxymethyl cellulose, and polyvinyl alcohol, etc.

Preferable examples of colorants include: water-soluble edible tartrazine dyes (edible dye such as edible Red No.2 and No.3, edible Yellow No.4 and No.5, edible Blue No.1 and No.2); water-insoluble lake dyes (such as aluminum salt of the above water-soluble edible tartrazine dyes); and natural dyes (such as β-carotene, chlorophyll and colcothar), etc.

Preferable examples of sweetening agents include: saccharin sodium, glycyrrhetinic acid, aspartame and stevioside, etc.

Generally, the method for preparing the tablets comprises pressing or molding the pharmaceutical composition of the present invention with one or more pharmaceutically acceptable vehicles.

The pharmaceutical composition of the present invention can also be formulated into oral liquid preparations, for instance, water-soluble or oil-soluble suspensions, solutions, emulsions, syrups, etc. The pharmaceutical composition of the present invention can also be a dry product, which is re-blended with water or other suitable carriers before use. This sort of liquid preparations can contain conventional additives, including suspending agents, such as sorbitol syrup, methylcellulose, glucose/syrup, gelatin, hydroxyethyl cellulose, carboxymethyl cellulose, aluminum stearate gel or hydrogenated edible fat; emulsifying-agents, such as lecithin, sorbitan monoleate or arabic gum; non-aqueous carriers which can include edible oil, such as almond oil, fractionated coconut oil, butyraceous esters, propylene glycol or ethanol; and preservatives, such as methyl paraben, nipasol and sorbic acid. If necessary, conventional scenting agents or colorants can be included.

The preparations for parenteral administration include aqueous and non-aqueous sterile injections, wherein, these preparations can contain antioxidants, buffering agents, bacteriostatic agents and isotonic agents, etc; and the preparations for parenteral administration can include aqueous and non-aqueous sterile suspensions, wherein, these preparations can contain suspending-agents and thickening agents. The preparations can be preserved in single-dose or multi-dose vessels, such as sealed ampoules and vials, and can be stored under freeze-drying (lyophilization) conditions, only needing to be added with sterile liquid carriers, for example, water for injection, before use.

The preparations for rectal administration can be suppositories containing conventional suppository bases, for example, cocoa butter, stearic acid, or other glycerides or ethylene glycol.

The preparations for oral topical administration, for example, preparations for buccal or sublingual administration, include troches, wherein the active ingredient is embedded in a flavored base such as sucrose and arabic gum; and pastilles, wherein the active ingredient is embedded in a base such as gelatin and glycerol, or sucrose and arabic gum.

The pharmaceutical composition of the present invention can also be formulated into reservoir-type preparations, and such prolonged action preparation can be administered by implantation (such as subcutaneous or intramuscular implantation) or intramuscular injection. Therefore, the pharmaceutical composition of the present invention can be prepared with suitable polymers, or hydrophobic materials (for example emulsions in an acceptable oil), or ion-exchange resins, or prepared into a slightly-soluble derivative, for example, a slightly-soluble salt.

The present invention also describes use of the pharmaceutical composition of the invention in the preparation of a medicament for treating coronary heart disease.

The present invention also describes use of the pharmaceutical composition of the invention in the preparation of a medicament for improving myocardial damage, especially myocardial damage caused by heart failure.

The present invention also describes use of the pharmaceutical composition of the invention in the preparation of a medicament for treating or preventing heart failure, wherein the heart failure is preferably heart failure with reduced ejection fraction and/or heart failure with preserved ejection fraction.

The pharmaceutical composition of the present invention can inhibit the myocardial fibrosis and/or myocardial cell apoptosis and/or inflammatory response after heart failure.

The present invention describes a method for improving myocardial damage, comprising administering an effective amount of the pharmaceutical composition of the present invention to a subject having or at risk of having myocardial damage, wherein the myocardial damage is preferably myocardial damage caused by heart failure.

The present invention describes the above pharmaceutical composition of the present invention for improving myocardial damage, wherein the myocardial damage is preferably myocardial damage caused by heart failure.

The present invention describes a method of treating or preventing heart failure, comprising administering an effective amount of the pharmaceutical composition of the present invention to a subject having or at risk of having heart failure, wherein the heart failure is preferably heart failure with reduced ejection fraction and heart failure with preserved ejection fraction.

The present invention also describes the above pharmaceutical composition of the present invention for treating or preventing heart failure, wherein the heart failure is preferably heart failure with reduced ejection fraction and heart failure with preserved ejection fraction.

DETAILED DESCRIPTION OF THE INVENTION

Figure 1:
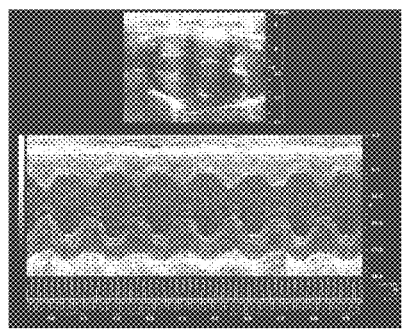
FIG. 1 is a representative image of M-mode ultrasound measured on day 28, representing the effects of each experimental group on rats with LAD-induced heart failure in terms of left ventricular function measured by echocardiogram.
Figure 1:
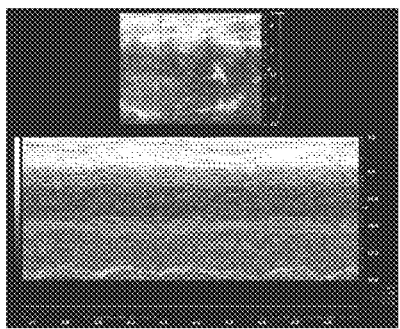
Figure 1:
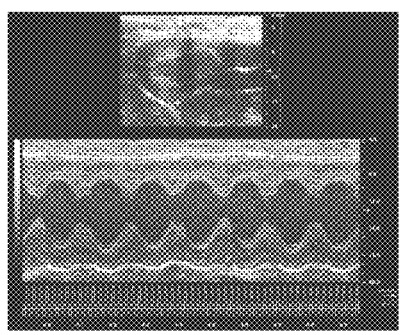
Figure 1:
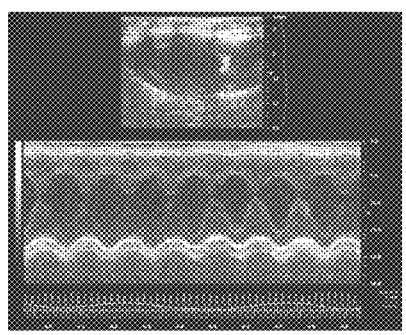

The specific embodiments of the present invention will be described in detail below with reference to the drawings, but it should be understood that the protection scope of the present invention is not limited by the specific embodiments.

Unless otherwise expressly stated, in the entire description and claims, the term "including" or variations thereof such as "comprising" and the like should be understood as including the stated elements or components, without excluding other elements or components.

EXAMPLES

Example 1

16 g of phenolic acids, 3.5 g of flavonoids, 0.2 g of tanshinones, and 16 g of saponins were uniformly mixed, and then uniformly mixed with 16 g of volatile oils to give a pharmaceutical composition.

The pharmaceutical composition comprises 11.55 g of Danshensu, 0.15 g of protocatechuic aldehyde, 0.6 g of salvianolic acid T, 0.6 g of salvianolic acid U, 1.3 g of salvianolic acid D, 0.05 g of salvianolic acid G, 0.8 g of rosmarinic acid, 0.4 g of lithospermic acid, 0.4 g of salvianolic acid B, 0.12 of salvianolic acid A, 0.04 g of isosalvianolic acid C, 2.1 g of calycosin-7-glucoside, 0.8 g of ononin, 0.2 g of calycosin, 0.78 g of formononetin, 0.048 g of dihydrotanshinone I, 0.064 g of cryptotanshinone, 0.04 g of tanshinone I, 0.048 g of tanshinone IIA, 3 g of notoginsenoside R1, 4.6 g of ginsenoside Rg1, 4.3 g of ginsenoside Rb1, 0.52 g of astragaloside, 0.52 g of ginsenoside Rd, 5.3 g of trans-nerolidol, 0.84 g of (3R,6S,7R)-3,7,11-trimethyl-3,7-epoxy-1,10-dodecadien-6-ol, 0.98 g of (3R,6R,7S)-3,7,11-trimethyl-3,7-epoxy-1,10-dodecadien-6-ol, 4.63 g of (3S,6R,7S)-3,7,11-trimethylt-3,6-epoxy-1,10-dodecadien-7-ol, 4.21 g of (3S,6S,7R)-3,7,11-trimethylt-3,6-epoxy-1,10-dodecadien-7-ol.

Example 2

15.36 g of phenolic acids, 3.33 g of flavonoids, 0.13 g of tanshinones, and 18.6 g of saponins were uniformly mixed, and then uniformly mixed with 16 g of volatile oils to give a pharmaceutical composition.

The pharmaceutical composition comprises 11 g of Danshensu, 0.15 g of protocatechuic aldehyde, 0.55 g of salvianolic acid T, 0.55 g of salvianolic acid U, 1.3 g of salvianolic acid D, 0.05 g of salvianolic acid G, 0.8 g of rosmarinic acid, 0.4 g of lithospermic acid, 0.4 g of salvianolic acid B, 0.12 g of salvianolic acid A, 0.04 g of isosalvianolic acid C, 1.8 g of calycosin-7-glucoside, 0.7 g of ononin, 0.18 g of calycosin, 0.65 g of formononetin, 0.03 g of dihydrotanshinone I, 0.04 g of cryptotanshinone, 0.025 g of tanshinone I, 0.03 g of tanshinone IIA, 3.5 g of notoginsenoside R1, 5.4 g of ginsenoside Rg1, 5 g of ginsenoside Rb1, 0.6 g of astragaloside, 0.6 g of ginsenoside Rd, 5.3 g of trans-nerolidol, 0.84 g of 0.84 g of (3R,6S,7R)-3,7,11-trimethyl-3,7-epoxy-1,10-dodecadien-6-ol, 0.98 g of (3R,6R,7S)-3,7,11-trimethyl-3,7-epoxy-1,10-dodecadien-6-ol, 4.63 g of (3S,6R,7S)-3,7,11-trimethylt-3,6-epoxy-1,10-dodecadien-7-ol, 4.21 g of (3S,6S,7R)-3,7,11-trimethylt-3,6-epoxy-1,10-dodecadien-7-ol

Example 3

4.42 g of phenolic acids, 0.96 g of flavonoids, 0.012 g of tanshinones, and 6.3 g of saponins were uniformly mixed, and then uniformly mixed with 15 g of volatile oils to give a pharmaceutical composition.

The pharmaceutical composition comprises 3 g of Danshensu, 0.06 g of protocatechuic aldehyde, 0.2 g of salvianolic acid T, 0.2 g of salvianolic acid U, 0.4 g of salvianolic acid D, 0.02 g of salvianolic acid G, 0.3 g of rosmarinic acid, 0.05 g of lithospermic acid, 0.1 g of salvianolic acid B, 0.07 g of salvianolic acid A, 0.015 g of isosalvianolic acid C, 0.6 g of calycosin-7-glucoside, 0.3 g of ononin, 0.03 g of calycosin, 0.03 g of formononetin, 0.001 g of dihydrotanshinone I, 0.005 g of cryptotanshinone, 0.002 g of tanshinone I, 0.004 g of tanshinone IIA, 1.8 g of notoginsenoside R1, 2.5 g of ginsenoside Rg1, 1.3 g of ginsenoside Rb1, 0.3 g of astragaloside, 0.4 g of ginsenoside Rd, 6.8 g of trans-nerolidol, 0.82 g of (3R,6S,7R)-3,7,11-trimethyl-3,7-epoxy-1,10-dodecadien-6-ol, 1.09 g of (3R,6R,7S)-3,7,11-trimethyl-3,7-epoxy-1,10-dodecadien-6-ol, 6.82 g of (3S,6R,7S)-3,7,11-trimethyl-3,6-epoxy-1,10-dodecadien-7-ol, 6.27 g of (3S,6S,7R)-3,7,11-trimethyl-3,6-epoxy-1,10-dodecadien-7-ol.

Example 4

18 g of phenolic acids, 4 g of flavonoids, 0.3 g of tanshinones, and 18 g of saponins were uniformly mixed, and then uniformly mixed with 16 g of volatile oils to give a pharmaceutical composition.

In the pharmaceutical composition, the phenolic acids comprise substances of the following weight parts: Danshensu:protocatechuic aldehyde:salvianolic acid T:salvianolic acid U:salvianolic acid D:salvianolic acid G:rosmarinic acid:lithospermic acid:salvianolic acid B:salvianolic acid A:isosalvianolic acid C=11:0.15:0.55:0.55:1.3:0.05:0.8:0.40:0.40:0.12:0.04; the flavonoids comprise substances of the following weight parts: calycosin-7-glucoside:ononin:calycosin:formononetin=1.8:0.7:0.18:0.65; the tanshinones comprise substances of the following weight parts: dihydrotanshinone I:cryptotanshinone:tanshinone I:tanshinone IIA=0.03:0.04:0.025:0.03. The saponins comprise substances of the following weight parts: notoginsenoside R1:ginsenoside Rg1:ginsenoside Rb1:astragaloside:ginsenoside Rd=3.5:5.4:5.0:0.60:0.6. The volatile oils comprise substances of the following weight parts: tans-nerolidol:(3R,6S,7R)-3,7,11-trimethyl-3,7-epoxy-1,10-dodecadien-6-ol:(3R,6R,7S) -3,7,11-trimethyl-3,7-epoxy-1,10-dodecadien-6-ol:(3S,6R,7S)-3 ,7,11-trimethyl-3,6-epoxy-1,10-dodecadien-7-ol:(3S,6S,7R)-3,7,11-trimethyl-3,6-epoxy-1,10-dodecadien-7-ol=38:6:7:33:30.

Example 5

18 g of phenolic acids, 4 g of flavonoids, 0.3 g of tanshinones, and 18 g of saponins were uniformly mixed, and then uniformly mixed with 17 g of volatile oils to give a pharmaceutical composition.

In the pharmaceutical composition, the phenolic acids comprise substances of the following weight parts: Danshensu:protocatechuic aldehyde:salvianolic acid T:salvianolic acid U:salvianolic acid D:salvianolic acid G:rosmarinic acid:lithospermic acid:salvianolic acid B:salvianolic acid A:isosalvianolic acid C=3:0.06:0.2:0.02:0.4:0.02:0.3:0.05: 0.1:0.07:0.015; the flavonoids comprise substances of the following weight parts: calycosin-7-glucoside:ononin:calycosin:formononetin=0.6:0.3:0.03:0.03; the tanshinones comprise substances of the following weight parts: dihydrotanshinone I:cryptotanshinone:tanshinone I:tanshinone IIA=0.001:0.005:0.002:0.004. The saponins comprise substances of the following weight parts: notoginsenoside R1:ginsenoside Rg1:ginsenoside Rb1:astragaloside:ginsenoside Rd=1.8:25:1.3:0.3:0.4. The volatile oils comprise substances of the following weight parts: trans-nerolidol: (3R,6S,7R)-3,7,11-trimethyl-3,7-epoxy-1,10-dodecadien-6-ol:(3R,6R,7S) -3,7,11-trimethyl-3,7-epoxy-1,10-dodecadien-6-ol : (3S,6R,7S)-3,7,11-trimethyl-3,6-epoxy-1,10-dodecadien-7-ol:(3S,6S,7R)-3,7,11-trimethyl-3,6-epoxy-1,10-dodecadien-7-ol=25:3:4:25:23.

Example 6

20 g of phenolic acids, 5 g of flavonoids, 0.5 g of tanshinones, and 20 g of saponins were uniformly mixed, and then uniformly mixed with 18 g of volatile oils to give a pharmaceutical composition.

In the pharmaceutical composition, the phenolic acids comprise substances of the following weight parts: Danshensu:protocatechuic aldehyde:salvianolic acid T:salvianolic acid U:salvianolic acid D:salvianolic acid G:rosmarinic acid:lithospermic acid:salvianolic acid B:salvianolic acid A:isosalvianolic acid C=11:0.15:0.55:0.55:1.3:0.05:0.8: 0.40:0.40:0.12:0.04; the flavonoids comprise substances of the following weight parts: calycosin-7-glucoside:ononin: calycosin:formononetin=1.8:0.7:0.18:0.65; the tanshinones comprise substances of the following weight parts: dihydrotanshinone I:cryptotanshinone:tanshinone I:tanshinone IIA=0.03:0.04:0.025:0.03. The saponins comprise substances of the following weight parts: notoginsenoside R1:ginsenoside Rg1:ginsenoside Rb1:astragaloside:ginsenoside Rd=3.5:5.4:5.0:0.60:0.6. The volatile oils comprise substances of the following weight parts: trans-nerolidol: (3R,6S,7R)-3,7,11-trimethyl-3,7-epoxy-1,10-dodecadien-6-ol:(3R,6R,7S) -3,7,11-trimethyl-3,7-epoxy-1,10-dodecadien-6-ol:(3S,6R,7S)-3,7,11-trimethyl-3,6-epoxy-1,10-dodecadien-7-ol:(3S,6S,7R)-3,7,11-trimethyl-3,6-epoxy-1,10-dodecadien-7-ol=38:6:7:33:30.

Example 7

2 g of phenolic acids, 0.5 g of flavonoids, 0.005 g of tanshinones, and 5 g of saponins were uniformly mixed, and then uniformly mixed with 10 g of volatile oils to give a pharmaceutical composition.

In the pharmaceutical composition, the phenolic acids comprise substances of the following weight parts: Danshensu:protocatechuic aldehyde:salvianolic acid T:salvianolic acid U:salvianolic acid D:salvianolic acid G:rosmarinic acid:lithospermic acid:salvianolic acid B:salvianolic acid A:isosalvianolic acid C=3:0.06:0.2:0.02:0.4:0.02:0.3:0.05: 0.1:0.07:0.015; the flavonoids comprise substances of the following weight parts: calycosin-7-glucoside:ononin:calycosin:formononetin=0.6:0.3:0.03:0.03; the tanshinones comprise substances of the following weight ratio: dihydrotanshinone I:cryptotanshinone:tanshinone I:tanshinone IIA=0.001:0.005:0.002:0.004. The saponins comprise substances of the following weight parts: notoginsenoside R1:ginsenoside Rg1:ginsenoside Rb1:astragaloside:ginsenoside Rd=1.8:25:1.3:0.3:0.4. The volatile oils comprise substances of the following weight parts: tans-nerolidol: (3R,6S,7R)-3,7,11-trimethyl-3,7-epoxy-1,10-dodecadien-6-ol:(3R,6R,7S) -3,7,11-trimethylt-3,7-epoxy-1,10-dodecadien-6-ol:(3S,6R,7S)-3,7,11-trimethyl-3,6-epoxy-1,10-dodecadien-7-ol:(3S,6S,7R)-3,7,11trimethyl-3,6-epoxy-1,10-dodecadien-7-ol=25:3:4:25:23.

Example 8

0.5 g of the pharmaceutical composition of Example 1 and 10.5 g of PEG-6000 were taken, mixed uniformly, melted by heating, and then transferred to a dropping tank. The liquid was dropped into a liquid paraffin at 6~8° C. to give 400 drop pills after the remaining paraffin being removed.

Example 9

0.5 g of the pharmaceutical composition of Example 2, 4.5 g of glucose, 0.9 g of sodium thiosulfate and 1 mL of distilled water were taken, mixed uniformly, lyophilized, and loaded separately into 500 vials, to give powders for injection.

Example 10

0.5 g of the pharmaceutical composition of Example 2, 5.5 g of mannitol, 0.9 g of calcium disodium edetate and 2 mL of distilled water were taken, mixed uniformly, lyophilized, and loaded separately into 300 vials, to give powders for injection.

Example 11

0.5 g of the pharmaceutical composition of Example 2, 50 g of starch and 50 g of sucrose were taken, mixed uniformly, granulated and pressed to give tablets.

Example 12

0.5 g of the pharmaceutical composition of Example 2, 50 g of starch and 50 g of sucrose were taken, mixed uniformly, granulated and loaded into capsule shells to give capsules.

Test Examples

The beneficial effects of the present invention were illustrated through the following test examples.

Test Example 1

Heart Failure with Reduced Ejection Fraction
1. Animal Model and Administration Mode
1.1 Experimental Animals All animals were approved by Management of Center for Laboratory Animal of Tianjin University of Traditional Chinese Drug (TCM-LAEC2017003). SD male rats of clean grade weighing 200±20 g were selected and fed at a temperature of 22-25° C. and a humidity of 40-70%. The rats were provided with light day and night during feeding, regularly fed with standard pellet feed, provided with sterilized drinking water, and subjected to test after one week of adaptive feeding in the experimental environment.

1.2 Experimental Drugs

Drug group of the present invention: the pharmaceutical composition of Example 2 (QSYQ-1), 169 g.

Comparison drug group: the pharmaceutical composition of Example 2 without volatile oils (QSYQ-2), 169 g.

1.3 Experimental Methods

The rats were fasted for 12 hours before surgery except for free access to water. The weights of the rats were recorded, and the rats were anesthetized with 5% chloral hydrate (6 mL/kg) by intraperitoneal injection. After the rats were under anesthesia (about 2-5 mins, no pain responses occurred when the rats' toes were pinched by hands), the following operations were performed.

The prethoracic operation area was sterilized with iodophor alcohol, and an incision of approximate 5 mm in length was made between the third and fourth ribs of the left chest of the rat. The muscle layers were separated bluntly, and the chest cavity was opened between the third and fourth ribs with a hemostatic forcep and pulled with a pulling hook to expose the chest cavity. Under the visual field of a stereomicroscope, the position of the heart was determined, and the pericardium was cautiously torn to determine the position of the left anterior descending coronary artery (at the junction of the pulmonary conus and the left atrial appendage). Ligation was performed using a 5-0 gauge of silk thread with needle at a distance of 2-3 mm below the starting point of the coronary artery at the root of the left atrial appendage. After the ligation, it could be seen by a naked eye that the corresponding area on the surface of the heart turned pale from bright red, and myocardial cyanosis appeared in the supply range of the blood vessels; the heart rate of the rat significantly accelerated, and the breathing was rapid, with reduced degree of heartbeats. The pulling hook was loosened, and the liquid remaining in the chest cavity was sucked with a cotton swab. Gas in the chest cavity was squeezed out, and the muscles and skins were quickly sutured with a 3-0 gauge of thread. The rat after the surgery was placed on an electric blanket. After the rat resumed spontaneous breathing, the trachea intubation was pulled out, and the rat was administrated with penicillin after the surgery. Wherein, the sham operation group was only threaded under the anterior descending coronary artery without ligation, and the rest of the treatment was the same as above.

Until 12-13 days after modeling, the rats were subjected to echocardiography respectively to evaluate whether the modeling was successful. The successful modeled rats were randomly divided into four groups, namely the model group, the sham operation group (i.e., the blank control group in the cell experiment), the pharmaceutical composition group of the present invention, and the comparison drug group of the present invention respectively. In the pharmaceutical composition group of the present invention, from 14 days after the surgery, the rat was gavaged with QSYQ-1 daily at a clinical equivalent dose of 100 mg/kg for 14 days based on the clinical daily dosage for humans. In the comparison drug group (QSYQ-2), from 14 days after the surgery, the rat was gavaged daily at a clinical equivalent dose of 100 mg/kg for 14 days based on the clinical daily dosage for humans.

2. Sample Collection

Blood sample: after the hemodynamic test, the blood was taken from the abdominal aorta of the rat, and then the tube with the blood was marked at the mouth thereof, placed in a 37° C. water bath for 30 mins, and centrifuged at 3000 rpm for 15 mins. The serum was taken, divided into 1.5 mL shell tubes, and stored at −80° C. for further use.

Heart sample: it was performed after the blood was taken from the abdominal aorta. The heart was cut off after the blood was taken, rinsed twice with a 4% paraformaldehyde solution, placed in a formalin solution for fixation, and stored for further use.

3. Animal Model Evaluation

Ultrasound evaluation: echocardiographic evaluation of the rat was performed at 14 days after surgery, and the heart failure modeling was identified as success when the EF value was within the range of 38-50%. Double antibody sandwich enzyme-linked immunosorbent assay (ELISA) was applied to detect the levels of TNF-α, IL-6 and IL1-β in the serum samples. An automatic biochemical analyzer was applied to detect CK, CK-MB and LDH.

The heart samples were dehydrated, embedded and sectioned, and the sections were stained by HE staining and TUNEL fluorescence staining.

4. Statistics

The experimental data were statistically processed with SPSS22.0 software, and the experimental results were expressed as mean±standard deviation ($\bar{x}\pm s$). One-way analysis of variance (one-way ANOVA) was used for comparison between groups, and $P<0.05$ means the difference had statistical significance. Data in the figure were shown as the mean±standard deviation ($\bar{x}\pm SD$).

5. Results 5.1 Effects of Each Treatment Group on the Heart Function of Rats

The results of the ultrasound evaluation of M-Mode showed that, compared with the normal control group, the ventricular cavity of the model group was progressively dilated, and the movement of the left ventricular wall was weakened, and the contractility was decreased. However, after QSYQ-1 and QSYQ-2 were administered, both the degrees of dilation and contractility of the ventricular cavity were improved, as shown in FIG. 1 (the representative image of M-mode ultrasound). After the ligation of the left anterior descending coronary artery was modeled, the ejection fraction, fractional shortening and left ventricular area change score of the rats were significantly reduced compared with those of the normal control group (i.e., sham operation group). After treatments with each drug group, the rates of continuous decrease of the left ventricular ejection fraction of the rats in the administration groups were limited compared with those of the model group, and the differences were statistically significant. The change of the left ventricular fractional shortening was consistent with the left ventricular ejection fraction, and the difference in FS value was statistically significant compared with that of the model group. Each experimental group (QSYQ-1 and QSYQ-2) had protective effects on the heart function of the rats with heart failure induced by LAD. The data of the ejection fraction (EF) and fractional shortening (FS) were measured from day 28, see Tables 1 and 2. Both the EF and FS of QSYQ-1 were higher than those of QSYQ-2, indicating that the volatile oils in the composition of the present invention had effects of promoting absorption of compositions of salvianolic acids, saponins, flavonoids and tanshinones, and synergistically played protection functions on the heart function of patients with heart failure.

TABLE 1

Ejection fraction (EF) of rats in each administration group

| Group | Sham operation group | Model group | QSYQ-1 | QSYQ-2 |
|---|---|---|---|---|
| 1 | 89.3 | 38.1 | 69.0 | 65.8 |
| 2 | 75.1 | 42.2 | 57.9 | 75.7 |
| 3 | 82.1 | 27.0 | 78.0 | 46.5 |
| 4 | 81.4 | 43.6 | 56.4 | 42.2 |
| 5 | 88.6 | 43.1 | 77.2 | 51.2 |
| 6 | 81.2 | 22.8 | 52.5 | 72.8 |
| 7 | 77.5 | 31.9 | 66.7 | 72.2 |
| 8 | 75.4 | 29.0 | 57.2 | 58.8 |
| Mean | 81.3 | 34.7 | 64.4 | 60.6 |
| SD | 5.1 | 7.6 | 9.2 | 12.1 |

TABLE 2

Fractional shortening (FS) of rats of each administration group

| Group | Sham operation group | Model group | QSYQ-1 | QSYQ-2 |
|---|---|---|---|---|
| 1 | 60.0 | 19.5 | 20.7 | 36.9 |
| 2 | 45.2 | 15.7 | 40.0 | 18.3 |
| 3 | 51.9 | 21.7 | 31.3 | 24.4 |
| 4 | 50.9 | 13.3 | 46.7 | 21.6 |
| 5 | 60.0 | 22.4 | 30.3 | 27.6 |
| 6 | 50.6 | 22.4 | 46.7 | 42.7 |
| 7 | 47.3 | 11.2 | 28.4 | 42.5 |
| 8 | 45.5 | 13.9 | 38.4 | 39.9 |
| Mean | 51.4 | 17.5 | 35.3 | 31.7 |
| SD | 5.5 | 4.2 | 8.6 | 9.2 |

5.2 Results of Myocardial Enzymological Indicators

The effects of each experimental group (QSYQ-1 and QSYQ-2) on myocardial enzyme release and myocardial histology in LAD-induced heart failure rats were investigated. The levels of CK, LDH, and CK-MB in the serum of the rats in the administration groups (i.e., QSYQ-1 and QSYQ-2) were all reduced compared with those of the model group, indicating that the administration groups had an effect of reducing myocardial enzyme. For the level of creatine kinase (CK), QSYQ-1 and QSYQ-2 were similar, while the reduction effects on creatine kinase MB isoenzyme (CK-MB) level and lactate dehydrogenase (LDH) level of QSYQ-1 were superior than those of QSYQ-2. It can be seen that the volatile oils of the drug group of the present invention have a synergistic effect. See Tables 3, 4, and 5.

TABLE 3

Creatine kinase (CK) levels in the serum of rats in each administration group

| Group | Sham operation group | Model group | QSYQ-1 | QSYQ-2 |
|---|---|---|---|---|
| 1 | 1006 | 1428 | 922 | 924 |
| 2 | 749 | 977 | 740 | 606 |
| 3 | 1190 | 961 | 736 | 723 |
| 4 | 738 | 1391 | 728 | 802 |
| 5 | 969 | 1252 | 1060 | 1104 |
| 6 | 862 | 922 | 1045 | 941 |
| 7 | 762 | 956 | 609 | 1103 |
| 8 | 1027 | 1077 | 1077 | 728 |
| Mean | 913 | 1121 | 865 | 866 |
| SD | 152 | 193 | 171 | 171 |

TABLE 4

Creatine kinase MB isoenzyme (CK-MB) levels in the serum of rats in each administration group

| Group | Sham operation group | Model group | QSYQ-1 | QSYQ-2 |
|---|---|---|---|---|
| 1 | 1723 | 1907 | 1681 | 1442 |
| 2 | 1634 | 1746 | 1072 | 908 |
| 3 | 1405 | 1699 | 1280 | 1056 |
| 4 | 1553 | 2530 | 1016 | 1542 |
| 5 | 1956 | 1990 | 879 | 1860 |
| 6 | 1094 | 1887 | 1041 | 1405 |
| 7 | 1663 | 1846 | 1939 | 1972 |
| 8 | 1583 | 1997 | 789 | 719 |
| Mean | 1576 | 1950 | 1212 | 1363 |
| SD | 234 | 240 | 376 | 414 |

TABLE 5

Lactate dehydrogenase (LDH) levels in serum of rats in each administration group

| Group | Sham operation group | Model group | QSYQ-1 | QSYQ-2 |
|---|---|---|---|---|
| 1 | 1898 | 2356 | 1352 | 1734 |
| 2 | 999 | 1744 | 1321 | 1230 |
| 3 | 1645 | 1385 | 1285 | 1350 |
| 4 | 1615 | 2412 | 737 | 1551 |
| 5 | 1785 | 1853 | 1086 | 1437 |
| 6 | 899 | 1986 | 2066 | 1602 |
| 7 | 1545 | 1453 | 956 | 1389 |
| 8 | 1911 | 2052 | 1649 | 1152 |
| Mean | 1537 | 1905 | 1307 | 1431 |
| SD | 362 | 352 | 386 | 181 |

5.3 Pathological Results

Figure 2:
FIG. 2 is a representative image of HE staining (400× magnification), wherein the nuclei were marked in blue with DAPI.
Figure 2:
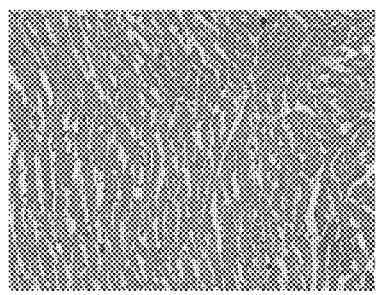
Figure 2:
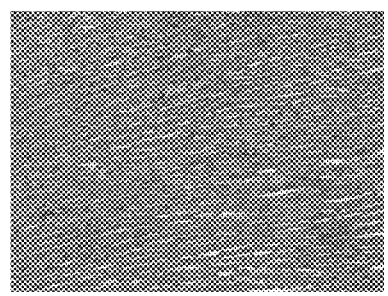
Figure 2:
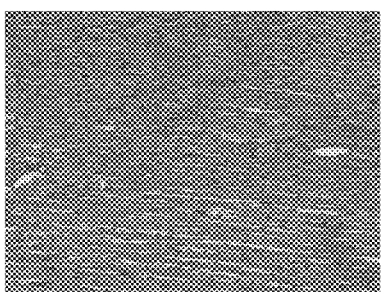

The results of HE staining were shown in FIG. 2, a representative image of HE staining (400× magnification), wherein the nuclei were marked in blue with DAPI. Compared with the normal sham operation group, the model group had significantly increased leukocyte infiltration and obvious myocardial fiber rupture. Each therapeutic and pre-interventional drug administrated group can significantly reduce the degree of myocardial damage.

Figure 3:
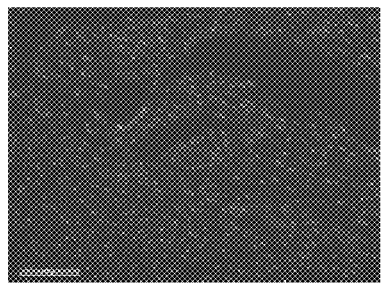
FIG. 3 is a representative micrograph of TUNEL staining (400× magnification), wherein the apoptotic nuclei were marked in green.
Figure 3:
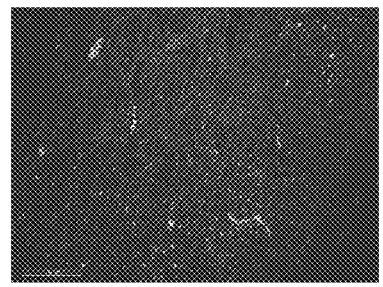
Figure 3:
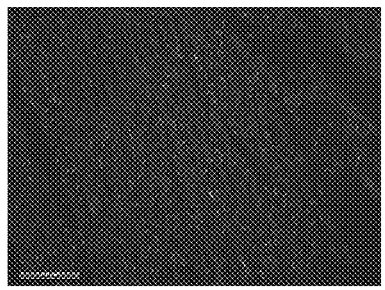
Figure 3:
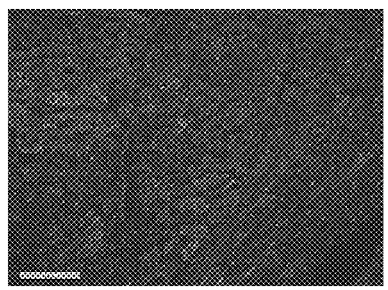

Tunel staining results were shown in FIG. 3, a representative micrograph of TUNEL staining (400× magnification), wherein the apoptotic cell nuclei were marked in green, showing that the ligation of the left anterior descending coronary artery can cause damage to the cardiomyocytes of the rats. From FIG. 2, obvious fluorescein-labeled apoptotic bodies can be observed after staining, and the apoptosis rate of the myocardial cell increased significantly compared with that of the normal sham operation group.

In summary, the studies in above items 5.1-5.3 showed that, in the heart failure rat model with the ligation of the left anterior descending coronary artery, the movement of the left ventricular anterior wall was greatly reduced, and the myocardial contractility was significantly reduced, indicating that the model group had a significant decrease in heart function compared with the sham operation group. QSYQ-1 can significantly alleviate the changes of the left ventricle, significantly slow down the continuous decrease in EF and FS values caused by the heart damage of the rats induced by the ligation of the left anterior descending coronary artery, maintain the myocardial contractility and ensure the blood supply of the heart. Myocardial enzymological experiment results showed that after the drug being administrated, the levels of CK, CK-MB and LDH in the model rats were reduced. Possibly due to the too long modeling time, the acute increase in the levels of these enzymes after myocardial damage will gradually recover with time. QSYQ-1 also showed an effect of reducing myocardial enzymes, indicating that a certain effect in heart protection can be achieved after the drug being administrated. In addition, the results of HE staining and Tunel showed that after the drug being administrated, inflammatory response, myocardial fibrosis and myocardial cell apoptosis and the like in the model rats after heart failure can be inhibited, thereby achieving the effect of protecting myocardial cells.

Test Example 2

Cell Culture and Activity Evaluation

1. Experimental drugs: drug group of the present invention (QSYQ-1) and comparison drug group (QSYQ-2) are the same as those of Test Example 1;

Active ingredient groups, each separately comprised one of the following: Danshensu, protocatechuic aldehyde, salvianolic acid T, salvianolic acid U, salvianolic acid D, salvianolic acid G, rosmarinic acid, lithospermic acid, salvianolic acid B, salvianolic acid A, isosalvianolic acid C, calycosin-7-glucoside, ononin, calycosin, formononetin, dihydrotanshinone I, cryptotanshinone, tanshinone I, tanshinone IIA, notoginsenoside R1, ginsenoside Rg1, ginsenoside Rb1, astragaloside, ginsenoside Rd.

The weight of each group was 160 g.

2. Experimental methods: QSYQ-1 and QSYQ-2, and each active ingredient group were ultrasonically dissolved and prepared into a 0.4 mg/mL of stock solution with DMSO. When in vitro activity evaluation was performed, the above groups were diluted with the same amount of experimental medium respectively.

The cells were collected at the logarithmic growth phase and added to a 96-well culture plate with a black transparent bottom at a concentration of 5000 cells per well and a volume of 100 μL per well. The cells were incubated in an incubator with 5% $CO_2$ at 37° C. for 24 hours. Subsequently, the tested groups were added to the experimental groups respectively, incubated for 24 hours, and then placed in a hypoxic chamber passing a mixed gas composed of 95% nitrogen and 5% $CO_2$ at a flow rate of 15 L/min for 10 mins, and incubated for another 8 hours after inducing hypoxia damage at 37° C. The model group was only incubated for 8 hours under hypoxia, and the blank control group was incubated normally.

The labeling operation of cell fluorescent probe was as follows: the mother liquor of fluorescent probe Hoechst 33342 was diluted 1000-fold into a DMEM basic medium; then the mother liquor of MitoTracker Deep Red FM was diluted 10000-fold into a culture medium containing Hoechst 33342 to serve as a "cocktail" stain. The medium in the culture plate was discarded and replaced with the "cocktail" stain, 50 μL per well, and incubated in an incubator away from light for 30 mins. The plate was taken out away from light, and washed with DMEM (high glucose) for 3 times and 5 minutes each time. Live cell imaging was performed subsequently.

The operation of live cell imaging with HCS was as follows: an excitation light of 360-400 and an emission light of 410-480 were selected for the imaging of Hoechst 33342-labeled nuclei; an excitation light of 620-640 and an emission light of 650-760 were selected for the imaging of MitoTracker Deep Red FM-labeled mitochondria. Harmony 3.0 software was applied to analyze the HCS imaging and read the fluorescence intensities of the nucleus/cytoplasm. The HCS screening system combined the automatic fluorescence microscopy imaging functions, and can perform a high-throughput multi-index analysis. Columbus high-efficiency image and data management and analysis system were applied to perform a secondary analysis and management of the image and data, and draw the dosage-dependent curve relationship.

Statistical method: the same as Test Example 1.

3. Experimental results: in the hypoxia-induced cardiomyocyte damage model of FIG. 4 and Table 6, the number of live cell nuclei was significantly reduced compared with that of the blank control group, while the pre-administration of QSYQ-1 in the experimental groups showed a significantly obvious protective effect, which was superior to the comparison drug group without the volatile oils (QSYQ-2). Table 7 showed the results of the protective effect of the single component in the drug of the present invention on H9c2 myocardial cell damage induced by hypoxia in terms of nucleus number. The phenolic acids, flavonoids, saponins, tanshinones in the drug group of the present invention all had a certain protective effect on the number of cardiomyocytes, but the effect of each component was inferior to the protective effect of the pharmaceutical composition of the present invention on myocardial cell damage, indicating that the drug group of the present invention can play a synergistic effect after combining these various components.

TABLE 6

Protective effects of each experimental group on H9c2 cardiomyocyte damage-induced by hypoxia in terms of nucleus number

| Group | Blank group | Model group | QSYQ-1 | QSYQ-2 |
|---|---|---|---|---|
| 1 | 683 | 383 | 499 | 451 |
| 2 | 694 | 286 | 562 | 532 |
| 3 | 684 | 418 | 618 | 541 |
| 4 | 758 | 391 | 577 | 571 |
| 5 | 605 | 351 | 541 | 497 |
| 6 | 658 | 352 | 557 | 463 |
| Mean | 680.3 | 363.5 | 559.0 | 509.2 |
| SD | 45.5 | 41.6 | 35.9 | 42.9 |

TABLE 7

Protective effects of the single component in the drug of the present invention on H9c2 cardiomyocyte damage induced by hypoxia in terms of nucleus number

| Group | Blank | Control | Drug group of the present invention | Danshensu | Protocatechuic aldehyde | Calycosin-7-glucoside |
|---|---|---|---|---|---|---|
| N1 | 583 | 318 | 562 | 371 | 345 | 366 |
| N2 | 594 | 291 | 518 | 342 | 303 | 323 |
| N3 | 584 | 351 | 477 | 326 | 361 | 312 |
| Mean | 604.8 | 339.0 | 519.0 | 346.3 | 336.3 | 333.7 |
| SD | 27.8 | 31.6 | 34.7 | 18.6 | 24.5 | 23.3 |
| Significance | | | | ** | ** | ** |

TABLE 7-continued

Protective effects of the single component in the drug of the present invention on H9c2 cardiomyocyte damage induced by hypoxia in terms of nucleus number

| Group | Salvianolic acid T | Salvianolic acid U | Salvianolic acid D | Salvianolic acid G | Rosmarinic acid | Lithospermic acid |
|---|---|---|---|---|---|---|
| N1 | 325 | 349 | 306 | 380 | 304 | 348 |
| N2 | 279 | 315 | 236 | 328 | 367 | 377 |
| N3 | 284 | 252 | 273 | 391 | 365 | 343 |
| Mean | 296.0 | 305.3 | 271.7 | 366.3 | 345.3 | 356.0 |
| SD | 20.6 | 40.2 | 28.6 | 27.5 | 29.2 | 15.0 |
| Significance | ** | ** | ** | ** | ** | ** |

| Group | Formononetin | Salvianolic acid B | Notoginsenoside R1 | Ginsenoside Rg1 | Calycosin | Salvianolic acid A |
|---|---|---|---|---|---|---|
| N1 | 373 | 385 | 360 | 264 | 435 | 264 |
| N2 | 362 | 364 | 383 | 310 | 381 | 287 |
| N3 | 394 | 435 | 355 | 350 | 342 | 254 |
| Mean | 376.3 | 394.7 | 366.0 | 308.0 | 386.0 | 268.3 |
| SD | 13.3 | 29.8 | 12.2 | 35.1 | 38.1 | 13.8 |
| Significance | ** | ** | ** | ** | ** | |

| Group | Isosalvianolic acid C | Ginsenoside Rb1 | Ononin | Astragaioside | Ginsenoside Rd | Dihydrotanshinone I |
|---|---|---|---|---|---|---|
| N1 | 293 | 406 | 305 | 374 | 436 | 303 |
| N2 | 326 | 420 | 394 | 365 | 407 | 373 |
| N3 | 293 | 386 | 399 | 435 | 381 | 313 |
| Mean | 304.0 | 404.0 | 366.0 | 391.3 | 408.0 | 339.7 |
| SD | 15.6 | 14.0 | 43.2 | 31.1 | 22.5 | 28.7 |
| Significance | ** | ** | ** | ** | ** | ** |

| Group | Cryptotanshinone | Tanshinone I | Tanshinone IIA |
|---|---|---|---|
| N1 | 329 | 379 | 391 |
| N2 | 365 | 315 | 373 |
| N3 | 353 | 300 | 416 |
| Mean | 349.0 | 331.3 | 393.3 |
| SD | 15.0 | 34.3 | 17.6 |
| Significance | ** | ** | ** |

Note:
** $P < 0.01$, compared with the drug group of the present invention;
* $P < 0.05$, compared with the drug group of the present invention.

Figure 4:
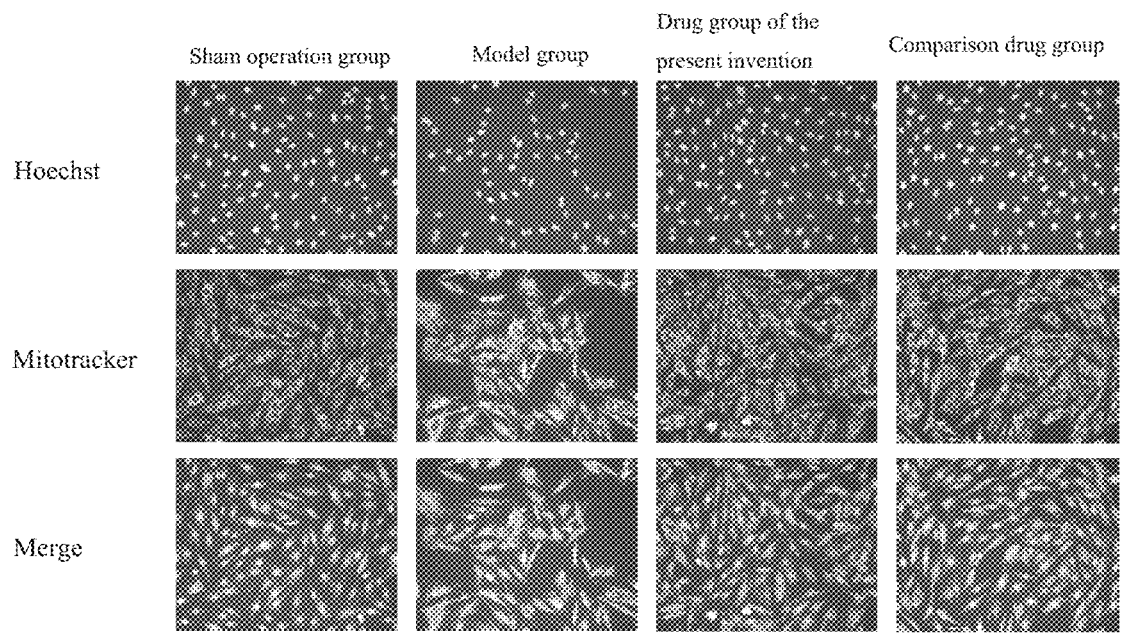
FIG. 4 represents the protective effects of each experimental group on hypoxia-induced H9c2 myocardial cell damage in terms of nucleus number and mitochondrial biological function. Fluorescent dyes are adopted for the high-content imaging of H9c2 cells in terms of nucleus number and mitochondrial quality. The nuclei are blue after being transfected with Hoechst fluorescent dye; the mitochondria are red after being transfected with Mitotracker fluorescent dye; Merge represents the image after the two being combined.

In terms of mitochondrial quality, compared with the blank control group, since the lack of oxygen supply after the myocardial hypoxia damage and the compensatory regulation of intracellular oxygen sensors for improving the oxygen utilization capacity, the model group in FIG. 4 and Table 8 had a significantly increased mitochondrial quality. While after being pre-administered with QSYQ-1, the experimental group showed a very significant protective effect, which was superior to the comparison drug group without the volatile oils (QSYQ-2). Table 9 showed the protective effects of the drug group of the present invention and the single component therein on H9c2 cardiomyocyte damage induced by hypoxia in terms of mitochondrial function. The results showed that the phenolic acids, flavonoids, saponins, tanshinones in the drug group of the present invention all had a certain protective effect on the mitochondrial function of myocardial cells, but the effect of each component was inferior to the protective effect of the pharmaceutical composition of the present invention on mitochondrial function after myocardial damage, indicating that the drug group of the present invention can play a synergistic effect after combining these various components.

TABLE 8

Protective effects of each experimental group on H9c2 cardiomyocyte damage induced by hypoxia in terms of mitochondrial biological function

| Group | Blank group | Model group | QSYQ-1 | QSYQ-2 |
|---|---|---|---|---|
| N1 | 359.05 | 809.89 | 731.37 | 804.63 |
| N2 | 349.46 | | 698.98 | 792.84 |
| N3 | 263.68 | 801.82 | 698.32 | 783.48 |
| N4 | 298.03 | 948.86 | 604.72 | 716.78 |
| N5 | 296.01 | 797.47 | 677.53 | 752.52 |
| N6 | 274.62 | 805.48 | 682.28 | 774.68 |
| Mean | 306.8 | 832.7 | 682.2 | 770.1 |
| SD | 35.7 | 58.2 | 42.4 | 31.8 |

TABLE 9

Protective effects of the drug group of the present invention and the single component therein on H9c2 cardiomyocyte damage induced by hypoxia in terms of mitochondrial function

| Group | Blank group | Model group | Drug group of the present invention | Danshensu | Protocatechuic aldehyde | Calycosin-7-glucoside |
|---|---|---|---|---|---|---|
| N1 | 359.05 | 809.89 | 563.39 | 882.04 | 901.89 | 877.99 |
| N2 | 349.46 | 801.82 | 605.09 | 909.24 | 946.04 | 967.77 |
| N3 | 263.68 | 948.86 | 628.9 | 845.81 | 881.05 | 861.05 |
| Mean | 306.8 | 832.7 | 599.1 | 879.0 | 909.7 | 902.3 |
| SD | 35.7 | 58.2 | 27.1 | 26.0 | 27.1 | 46.8 |
| Significance | | | | ** | ** | ** |

| Group | Salvianolic acid T | Salvianolic acid U | Salvianolic acid D | Saivianolic acid G | Rosinarinc acid | Lithospermic acid |
|---|---|---|---|---|---|---|
| N1 | 815.14 | 992.37 | 946.71 | 870.9 | 829.81 | 830.41 |
| N2 | 888.53 | 840.14 | 900.04 | 831.06 | 752.31 | 836.23 |
| N3 | 824.27 | 895.53 | 920.17 | 901.01 | 789.57 | 777.18 |
| Mean | 842.6 | 909.3 | 922.3 | 867.7 | 790.6 | 811.6 |
| SD | 32.7 | 62.9 | 19.1 | 28.6 | 31.6 | 26.6 |
| Significance | ** | ** | A* | ** | ** | ** |

| Group | Formononetin | Salvianolic acid B | Notoainsenoside R1 | Ginsenoside Rg1 | Calycosin | Saivianolic acid A |
|---|---|---|---|---|---|---|
| N1 | 902.44 | 801.62 | 841.9 | 843.46 | 997.59 | 914.19 |
| N2 | 881.15 | 853.39 | 950.39 | 918.73 | 874.12 | 859.26 |
| N3 | 807.47 | 910.53 | 985.33 | 954.27 | 845.03 | 941.93 |
| Mean | 863.7 | 855.2 | 925.9 | 905.5 | 905.6 | 905.1 |
| SD | 40.7 | 44.5 | 61.1 | 46.2 | 66.1 | 34.4 |
| Significance | ** | ** | ** | ** | ** | ** |

| Group | Isosalvianolic acid C | Ginsenoside Rb1 | Ononin | Astradaloside | Ginsenoside Rd | Dihydrotanshinone I |
|---|---|---|---|---|---|---|
| N1 | 766.96 | 778.78 | 659.1 | 812.45 | 892.87 | 930.1 |
| N2 | 812.08 | 843.1 | 684.73 | 768.63 | 836.92 | 918.77 |
| N3 | 738.89 | 822.04 | 741.02 | 871.37 | 732.79 | 813.04 |
| Mean | 772.6 | 814.6 | 695.0 | 817.5 | 820.9 | 887.3 |
| SD | 30.1 | 26.8 | 34.2 | 42.1 | 66.3 | 52.7 |
| Significance | ** | ** | * | ** | ** | ** |

| Group | Cryptotanshinone | Tanshinone I | Tanshinone IIA |
|---|---|---|---|
| N1 | 883.97 | 876.03 | 739.65 |
| N2 | 859.64 | 904.55 | 641.34 |
| N3 | 817.92 | 828.87 | 704.67 |
| Mean | 853.8 | 869.8 | 695.2 |
| SD | 27.3 | 31.2 | 10.7 |
| Significance | ** | ** | * |

Note:
** $P < 0.01$, compared with the drug group of the present invention;
* $P < 0.05$, compared with the drug group of the present invention.

4. Conclusion: the activity evaluations in Tables 6 to 9 showed that the QSYQ-1 had a significantly superior activity than the pharmaceutical composition consisting of 24 components (i.e., QSYQ-2) and every single component, and there was a synergistic effect between the pharmaceutical components of the present invention.

Test Example 3

Heart Failure with Preserved Ejection Fraction
Study on the Effectiveness of Continuous Administration of the Pharmaceutical Composition of the Present Invention for 90 Days on Rhesus Monkeys with Spontaneous Chronic Heart Failure 1. Study Purposes The study was to evaluate the effectiveness of continuous administration of the pharmaceutical composition of the present invention for 90 days at a clinically equivalent dose, and observe the spontaneous chronic heart failure (NYHA class II-IV, HfpEF) of rhesus monkey (middle-aged/aged). The main pharmacodynamic indicators were echocardiographic indicators for analyzing the heart structure and changes in contractile and diastolic functions before and after administration.

2. Experimental Materials and Methods
2.1 Experimental Materials
2.1.1 Experimental Animals
Animal species: Rhesus monkey
Level: common level. Quarantine was qualified before the test, including physical examination, two *Mycobacterium tuberculosis* tests, and tests on parasites, *Salmonella, Shigella* and B virus.

Animal identification: a stainless steel number plate engraved with Arabic numerals was worn on the neck ring, and a tattoo was made on the chest.

(1) Inclusion Criteria

Male, aged 12-23 years (equivalent to human adults aged 40-70 years);

Body weight: 9-13 kg;

NYHA class II-class IV; wherein half of the animals in each group were HFpEF;

HFpEF (with moderate damage or above): e'<8 or E/e'>10 (according to clinical diagnostic criteria);

(2) Exclusion Criteria

Grades 2 and 3 hypertension (SBP>140 mmHg, DBP>90 mmHg)

Animals with severe liver and kidney dysfunction, anemia, leukocytosis, thrombocytopenia, electrolyte disturbance and abnormal fluctuations in body weight.

Animals with obvious clinical abnormal symptoms or diseases in endocrine, immunity, blood clotting and urogenital tract.

Any history of other diseases that may affect the evaluation of drug efficacy.

2.1.2 Test Substances

The drug of the present invention (Example 1, QSYQ) was provided by Tasly Pharmaceutical Group Co., Ltd. For the convenience of administration, the drug was mixed with PEG at a certain ratio to prepare a dripping pill preparation for animal experiments, batch number: 20180215.

2.2 Experimental Groups and Administrations

The test was divided into 3 groups: control group, QSYQ (Low), QSYQ (High), with 4 animals in each group.

Administration route: nasal feeding administration, once a day.

Dosage calculation: the dosage for next week was calculated based on the body weight weighed every time.

Administration time: 08:00-10:00 daily administration.

See Table 10 below for details.

TABLE 10

Experimental groups and administrations

| Group Name | Dosage (mg/kg/time, by extract amount) | Animal numbers (N) |
|---|---|---|
| Control group | 0 | 4 |
| QSYQ (Low) | 14.3 | 4 |
| QSYQ (High) | 28.5 | 4 |

2.3 Detection Indicators

Primary pharmacodynamic indicators: the heart function of the monkeys with heart failure was measured before administration, and on the $30^{th}$, $60^{th}$, and $90^{th}$ days of administration. The left ventricular complex of the long-axis section of the left ventricle lateral to the sternum was taken to measure left ventricular end-systolic and end-diastolic diameter, and calculate left ventricular end-diastolic volume (LVEDV), left ventricular end-systolic volume (LVESV), stroke volume (SV), Ea value, E/Ea value and other parameters, so as to evaluate the effects of the pharmaceutical composition of the present invention on the contractile and diastolic function of the monkeys with heart failure.

Secondary pharmacodynamic indicators: respective changes in the blood pressure of the monkeys before administration, and on the $30^{th}$, $60^{th}$, and $90^{th}$ days of administration.

Routine observation: daily performances, such as activity amount, feed intake and body weight, of the animals during administration were observed.

3. Statistical Methods

All data were measurement data, and expressed as mean±standard deviation ($\bar{x}$±SD). SPSS11.5 software was used to compare the variance analysis between groups repeatedly measured (if the data did not obey spherical distribution, quadratic curve fitting analysis was applied). Inspection level α=0.05.

4. Experimental Results

1) Effects on the Blood Pressure of Rhesus Monkeys with Spontaneous Chronic Heart Failure The results of the study showed that the pharmaceutical composition of the present invention had a certain improvement effect on the systolic pressure of monkeys with heart failure, and the antihypertensive efficacy was dose-dependent. The results were shown in Table 11.

TABLE 11

Effects of the pharmaceutical composition of the present invention on the blood pressure of the monkeys with heart failure

| Group | Systolic pressure (mmHg) | | | |
|---|---|---|---|---|
| | Basic blood pressure | 30 days of administration | 60 days of administration | 90 days of administration |
| Control group | 138.85 ± 6.22 | 132.14 ± 5.21 | 130.28 ± 3.58 | 127.72 ± 5.12 |
| QSYQ (Low) | 137.12 ± 5.54 | 136.87 ± 6.15 | 134.55 ± 6.74 | 130.36 ± 6.28 |
| QSYQ (High) | 136.58 ± 8.35 | 132.45 ± 3.25 | 131.65 ± 4.12 | 126.31 ± 7.03 |

2) Effects on the Heart Function of Rhesus Monkeys with Spontaneous Chronic Heart Failure The results of the study showed that the pharmaceutical composition of the present invention had a statistically significant difference in the left ventricular ejection fraction of the monkeys with heart failure compared to the vehicle group, indicating that the pharmaceutical composition of the present invention had a certain effect on the left ventricular contractility of the monkeys with heart failure, and can improve the left heart function of the monkeys with heart failure to a certain extent. The results were shown in Table 12.

Figure 5:
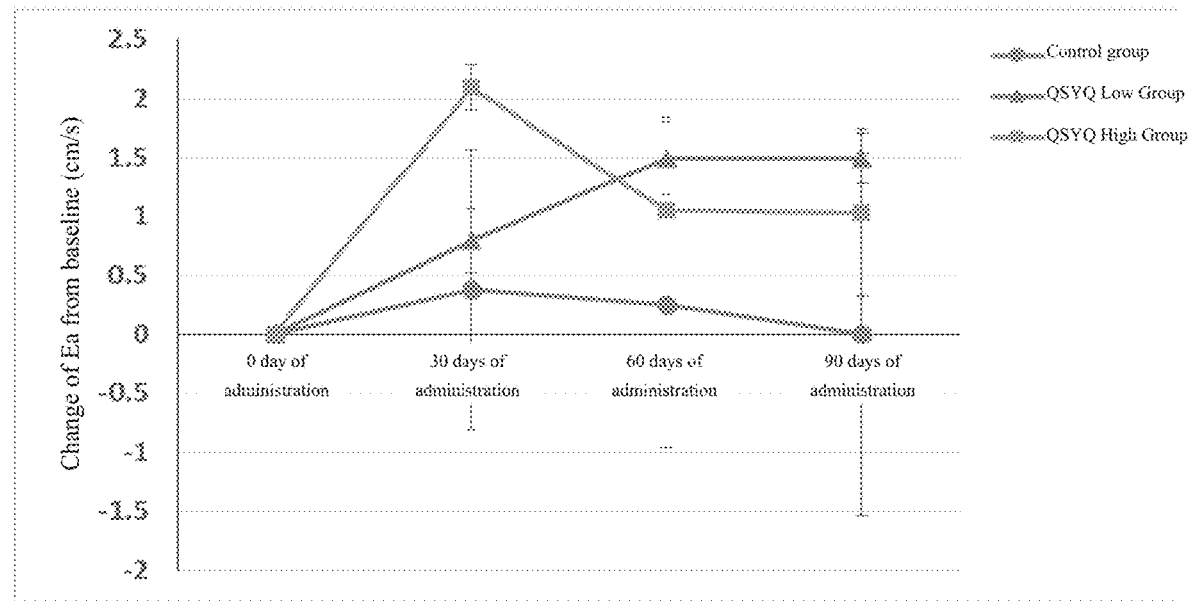
FIG. 5 represents the change in peak velocity of mitral annulus movement in early diastole (ΔEa) of each group during the administration of the drug of the present invention.
Figure 6:
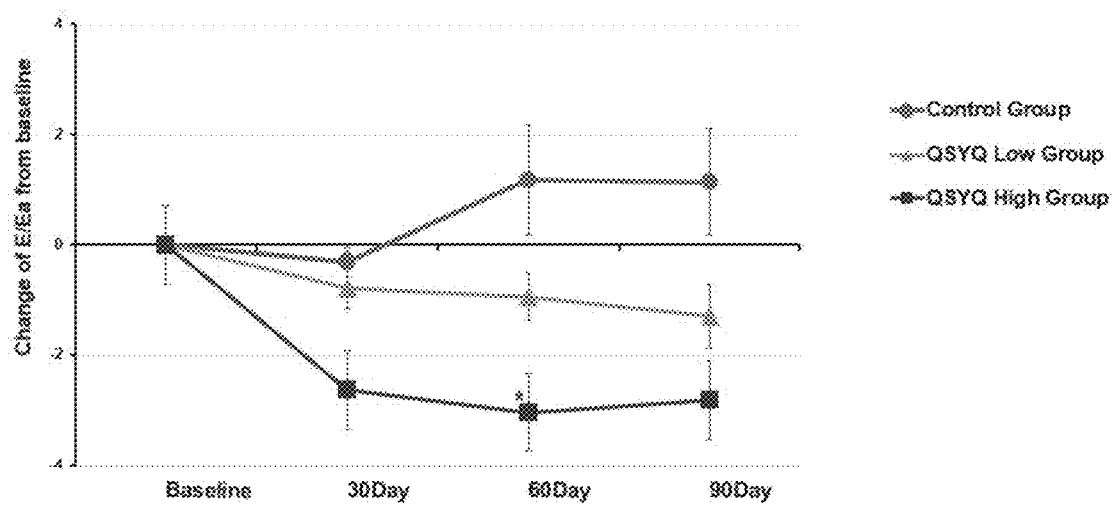
FIG. 6 represents the degree of change in the diastolic function E/Ea value (ΔE/Ea) of each group during the administration of the drug of the present invention.

In addition, for the detection of diastolic function, Ea and E/Ea are both commonly used parameters and sensitive indicators for evaluating the left ventricular diastolic function of the heart, and an E/Ea value of about 9 in monkeys is ideal. The study found that both the change in peak velocity of mitral annulus movement in early diastole (ΔEa) and the change in E/Ea (ΔE/Ea) of the administration group were better improved than those of the model group (see FIGS. 5 and 6).

TABLE 12

Effects of the pharmaceutical composition of the present invention on M-mode echocardiography of monkeys with heart failure after administration for 90 days

| | | M-mode echocardiography after administration for 90 days | |
|---|---|---|---|
| Indicators | Basic values | QSYQ (Low) | QSYQ (High) |
| LVEDV (ml) | 30.34 ± 2.01 | 31.27 ± 2.51 | 32.34 ± 3.22 |
| LVESV (ml) | 9.97 ± 2.41 | 8.78 ± 1.25 | 9.87 ± 2.02 |
| SV (ml) | 20.22 ± 3.03 | 20.33 ± 2.97 | 23.75 ± 2.58 |
| EF (%) | 61.51 ± 2.25 | 62.87 ± 3.13 | 70.25 ± 2.12* |
| FS (%) | 33.06 ± 3.11 | 32.15 ± 4.21 | 36.58 ± 1.96 |
| LVdMass(g) | 48.13 ± 4.01 | 48.55 ± 3.67 | 56.87 ± 1.58* |

Note:
*a significant difference compared with the basic value;
, a significant difference compared with the vehicle group in the same period.

3) Daily Observation

During the administration, the experimental animals were observed daily. It was found that the animals in the control group had less activity, and often had dyspnea, physical decline, debilitation, and less feed intake after activity. The animals of the pharmaceutical composition administrated group of the present invention (QSYQ) had more average daily activity than animals in control, were lively and active with good physical strength, and shortness of breath and other symptoms were rare, and the animal feed intake was normal.

5. Conclusion

The continuous administration of the pharmaceutical composition of the present invention for 90 days can increase the ejection fraction of the model monkey having heart failure with preserved ejection fraction, improve its contractile function, and also have a certain improvement effect on its diastolic function.

The foregoing descriptions of specific exemplary embodiments of the present invention have been presented for purposes of description and illustration. These descriptions are not intended to limit the invention to the precise forms disclosed, and obviously many variations and modifications can be made in light of the above teachings. The exemplary embodiments were chosen and described in order to explain certain principles of the invention and their practical application, to thereby enable the skilled in the art to make and utilize various exemplary embodiments of the present invention, as well as various alternatives and modifications thereof. It is intended that the scope of the invention be defined by the Claims appended hereto and their equivalents.

What is claimed is:

1. A pharmaceutical composition, comprising the following components:
Phenolic acids and aldehyde in an amount of 2-20 parts by weight;
Flavonoids in an amount of 0.5-5 parts by weight;
Tanshinones in an amount of 0.005-0.5 part by weight;
Saponins in an amount of 5-20 parts by weight; and
Volatile oils in an amount of 10-18 parts by weight; wherein
the phenolic acids are selected from Danshensu, protocatechuic aldehyde, salvianolic acid T, salvianolic acid U, salvianolic acid D, salvianolic acid G, rosmarinic acid, lithospermic acid, salvianolic acid B, salvianolic acid A, isosalvianolic acid C, or any combination thereof;
the flavonoids are selected from calycosin-7-glucoside, ononin, calycosin, formononetin, or any combination thereof;
the tanshinones are selected from dihydrotanshinone I, cryptotanshinone, tanshinone I, tanshinone IIA, or any combination thereof;
the saponins are selected from notoginsenoside R1, ginsenoside Rg1, ginsenoside Rb1, astragaloside, ginsenoside Rd, or any combination thereof;
the volatile oils are selected from trans-nerolidol, nerolidol oxide, or both; and
the nerolidol oxide, if presents, is selected from (3R,6S, 7R)-3,7,11-trimethyl-3,7-epoxy-1,10-dodecadien-6-ol, (3R,6R,7S)-3,7,11-trimethyl-3,7-epoxy-1,10-dodecadien-6-ol, (3S,6R,7S) 3,7,11-trimethyl-3,6-epoxy-1,10-dodecadien-7-ol, (3S,6S,7R)-3,7,11-trimethyl-3,6-epoxy -1,10-dodecadien-7-ol, or any combination thereof.

2. The pharmaceutical composition according to claim 1, wherein the composition comprises the following components:
Phenolic acids and aldehyde in an amount of 4-18 parts by weight;
Flavonoids in an amount of 0.8-4 parts by weight;
Tanshinones in an amount of 0.01-0.3 part by weight;
Saponins in an amount of 6-18 parts by weight; and
Volatile oils in an amount of 14-17 parts by weight.

3. The pharmaceutical composition according to claim 2, wherein the composition comprises the following components:
Phenolic acids and aldehyde in an amount of 6-16 parts by weight;
Flavonoids in an amount of 1-3 parts by weight;
Tanshinones in an amount 0.05-0.2 part by weight;
Saponins in an amount of 8-16 parts by weight; and
Volatile oils in an amount of 15-16 parts by weight.

4. The pharmaceutical composition according to claim 1, wherein the phenolic acids and aldehyde are selected from substances of the following weight parts: Danshensu: protocatechuic aldehyde:salvianolic acid T:salvianolic acid U:salvianolic acid D:salvianolic acid G:rosmarinic acid: lithospermic acid:salvianolic acid B:salvianolic acid A: isosalvianolic acid C=(3.0-11.0):(0.06-0.15):(0.2-0.55):(0.2-0.55):(0.4-1.3):(0.02-0.05):
(0.3-0.8):(0.05-0.40):(0.10-0.40):(0.07-0.12):(0.015-0.04).

5. The pharmaceutical composition according to claim 1, wherein the flavonoids are selected from substances of the following weight parts: calycosin-7-glucoside:ononin:calycosin:formononetin=(0.6-1.8):(0.3-0.7):(0.03-0.18):(0.03-0.65).

6. The pharmaceutical composition according to claim 1, wherein the tanshinones are selected from substances of the following weight parts: dihydrotanshinone I:cryptotanshinone:tanshinone I:tanshinone IIA=(0.001-0.03):(0.005-0.04):(0.002-0.025):(0.004-0.03).

7. The pharmaceutical composition according to claim 1, wherein the saponins are selected from substances with the following weight parts: notoginsenoside R1:ginsenoside Rg1:ginsenoside Rb1:astragaloside:ginsenoside Rd=(1.8-3.5):(2.5-5.4):(1.3-5.0):(0.30-0.60):(0.4-0.6).

8. The pharmaceutical composition according to claim 1, wherein the volatile oils are selected from substances with the following weight parts: trans -nerolidol:nerolidol oxide= (25-38):(55-76).

9. The pharmaceutical composition according to claim 8, wherein the nerolidol oxide are selected from (3R,6S,7R)-3,7,11-trimethyl-3,7-epoxy-1,10-dodecadien-6-ol, (3R,6R,7S)-3,7,11-trimethyl-3,7-epoxy-1,10-dodecadien-6-ol, (3S,6R,7S)-3,7,11-trimethylt-3,6-epoxy-1,10-dodecadien-7-ol, and (3S,6S,7R) -3,7,11-trimethylt-3,6-epoxy-1,10-dodecadien-7-ol, with the weight parts of (3-6):(4-7):(25-33):(23-30).

10. A pharmaceutically formulated preparation, comprising the pharmaceutical composition according to claim 1, wherein, the pharmaceutical composition accounts for 0.1~99.9 wt% of the pharmaceutically formulated preparation, and the remaining percentage is other pharmaceutically acceptable carrier(s).

11. The pharmaceutically formulated preparation according to claim 10, wherein the other pharmaceutically acceptable carriers are selected from the group consisting of: excipients, lubricants, adhesives, disintegrants, coating agents, colorants and sweetening agents.

12. The pharmaceutically formulated preparation according to claim 10, wherein the other pharmaceutically acceptable carriers are selected from the group consisting of: sugar alcohol, mannitol, sorbitol, xylitol; amino acid, cysteine hydrochloride, methionine, glycine, Vitamin C; EDTA disodium, EDTA calcium disodium salt, inorganic salts, monovalent alkali carbonate, acetate, phosphate or the aqueous solutions thereof, sodium chloride, potassium chloride, sodium pyrosulfite, sodium bisulfite, sodium thiosulfate; calcium carbonate, calcium bicarbonate; stearate, calcium stearate, magnesium stearate, inorganic acids, hydrochloric acid, acetic acid, sulfuric acid, phosphoric acid, organic acid salts, sodium lactate, oligosaccharide, polysaccharide, cellulose or the derivative thereof, maltose, glucose, fructose, dextran, sucrose, lactose, β-cyclodextrin, starch, silicon derivatives, alginate; gelatin, polyvinylpyrrolidone, glycerol; agar; surfactants, Tween-80, polyethylene glycol, phospholipids materials, Kaolin; and talc powder.

13. The pharmaceutically formulated preparation according to claim 10, wherein the pharmaceutically formulated preparation is in a dosage form selected from the group consisting of: tablets, sugar-coated tablets, film-coated tablets, and enteric-coated tablet, capsules, the group consisting of hard capsules, soft capsules, oral solutions; buccal tablets, granules, instant powders, pills, powders, pastes; pellets, suspensions, pulvis, solution, injections, suppositories, pastes, ointments, hard plasters, creams, sprays, drops, and patches.

14. The pharmaceutically formulated preparation according to claim 13, wherein the pharmaceutically formulated preparation is in a dosage form selected from the group consisting of: oral dosage forms, capsules, tablets, oral solutions, granules, pills, powders, pellets, pastes, injections, powders for injection, injection liquids and infusion.

15. The pharmaceutically formulated preparation according to claim 14, wherein the pharmaceutically formulated preparation in the oral dosage forms comprises the other pharmaceutically acceptable carriers selected from excipients, adhesives, bulking agents, diluents, table-pressing agents, lubricants, disintegrating agents, colorants, flavoring agents, wetting agents, or a combination of distinct agents thereof.

16. The pharmaceutically formulated preparation according to claim 15, wherein the bulking agents include: cellulose, mannitol, and/or lactose; the excipients include lactose, D-mannitol, D-sorbitol, starch, dextrin, crystalline cellulose, substituted hydroxypropyl cellulose, sodium carboxymethyl cellulose, arabic gum, amylopectin, anhydrous silicic acid, synthetic aluminum silicate, and/or aluminum magnesium silicate; the lubricants include magnesium stearate, calcium stearate, talc powder, silica gel, and/or sodium dodecyl sulfate.

17. The pharmaceutically formulated preparation according to claim 15, wherein the adhesives include α-starch, sucrose, gelatin, arabic gum, methylcellulose, carboxymethyl, sodium carboxymethyl cellulose, crystalline cellulose, sugar, D-mannitol, trehalose, dextrin, amylopectin, hydroxypropyl cellulose, hydroxypropyl methyl cellulose, or pyrrolidone; the disintegrating agents include lactose, sugar, starch, carboxymethyl cellulose, calcium carboxymethyl cellulose, sodium alkylamide, sodium carboxymethyl starch, anhydrous silicic acid, substituted hydroxypropyl celluose, starch, polyvinylpyrrolidone, or sodium starch glycolate.

18. The pharmaceutically formulated preparation according to claim 15, wherein the coating agents include hydroxypropyl methyl cellulose, hydroxypropyl cellulose, ethylcellulose, carboxymethyl cellulose, and/or polyvinyl alcohol; the colorants include: water-soluble edible tartrazine dyes, selected from one or more of edible Red No.2 and No.3, edible Yellow No.4 and No.5, and edible Blue No.1 and No.2; water-insoluble lake dyes, selected from aluminum salt of the water-soluble edible tartrazine dyes; and/or natural dyes, from one or more of β-carotene, chlorophyll and colcothar; selected sweetening agents include: saccharin sodium, glycyrrhetinic acid, aspartame, and/or stevioside.

19. A method for treating myocardial damage or heart failure, comprising administering an effective amount of the pharmaceutically formulated composition according to claim 1 or the pharmaceutical preparation according to claim 10 to a subject having myocardial damage, heart failure, or both.

* * * * *